(12) United States Patent
Sucov et al.

(10) Patent No.: US 7,189,510 B2
(45) Date of Patent: Mar. 13, 2007

(54) RESPONSE ELEMENT COMPOSITIONS AND ASSAYS EMPLOYING SAME

(75) Inventors: Henry M. Sucov, San Diego, CA (US); Ronald M. Evans, La Jolla, CA (US); Kazuhiko Umesono, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 163 days.

(21) Appl. No.: 10/302,557

(22) Filed: Nov. 22, 2002

(65) Prior Publication Data

US 2003/0099926 A1     May 29, 2003

Related U.S. Application Data

(60) Division of application No. 07/672,530, filed on Mar. 19, 1991, now Pat. No. 6,492,137, which is a continuation-in-part of application No. 07/438,757, filed on Nov. 16, 1989, now Pat. No. 5,091,518.

(51) Int. Cl.
*C12Q 1/68*     (2006.01)

(52) U.S. Cl. ............................ 435/6; 435/325; 536/24.1

(58) Field of Classification Search ...................... None
See application file for complete search history.

(56) References Cited

U.S. PATENT DOCUMENTS 5,262,300 A * 11/1993 Evans et al. .................... 435/6
6,281,330 B1 * 8/2001 Evans et al. ................. 530/324

FOREIGN PATENT DOCUMENTS

WO     WO 88/00975     2/1988
WO     WO 91/07488     5/1991

OTHER PUBLICATIONS

Lazar et al., "Thyroid hormone receptors form distinct nuclear protein-dependent and independent complexes with a thyroid hormone response element." Molecular Endocrinology, 4(11):Nov. 1990, p. 1627-1635.
Munoz-Canoves et al., "Mapping of a retinoic acid-responsive element in the promoter region of the complement factor H gene." Journal of Biological Chemistry, 265(33):Nov. 25, 1990, p. 20065-20068.
Sucov et al., "Characterization of an autoregulated response element in the mouse retinoic acid receptor type beta gene." Proceedings of the National Academy of Sciences USA, 87;Jul. 1990, p. 5392-5396.
Tsai et al., "Molecular Interactions of steroid hormone receptor with its enhancer element: evidence for receptor dimer formation." Cell, 55:Oct. 1988, p. 361-369.
Vasios et al., "A retinoic acid-responsive element is present in the 5' flanking region of the laminin B1 gene." Proceedings of the National Academy of Sciences USA, 86;Dec. 1989, p. 9099-9100.

* cited by examiner

*Primary Examiner*—James Ketter
(74) *Attorney, Agent, or Firm*—Foley & Lardner LLP; Stephen E. Reiter

(57) ABSTRACT

DNA segments have been discovered, and characterized by sequence, which are response elements operative to confer responsiveness to ligands for several members of the steroid/thyroid superfamily of receptors, for the transcriptional activation and/or repression of promoters in cells. By using transcriptional control regions comprising response elements of the present invention in combination with a functional promoter, it is now possible to provide recombinant DNA vectors containing a gene, the transcription (and, thereby, also expression) of which is under the control of a promoter, the transcriptional activity of which is responsive to ligands for members of the steroid/thyroid superfamily of receptors.

12 Claims, 5 Drawing Sheets

```
SacII
CCGCGGCGCT GGCTGAAGGC TCTTGCAGGG CTGCTGGGAG TTTTTAAGCG CTGTGAGAAT    60
                                                   SmaI
CCTGGGAGTT GGTGATGTCA GACTGGTTGG GTCATTTGAA GGTTAGCAGC CCGGGAAGGG   120
TTCACCGAAA GTTCACTCGC ATATATTAGG CAATTCAATC TTTCATTCCG TGTGACAGAA   180
GTGGTAGGAA GTGAGCTGCT CCGAGGCAGG AGGGTCTATT CTTTGCCAAA GGGGGGGACC   240
           SacII                                          SmaI
AGAGTTCCCG TGCGCCGCGG CCACAAGACT GGGATGCAGA GGACGCGAGC CACCCGGGCA   300
GGGAGCGTCT GGGCACCGGC GGGGTAGGAC CCGCGCGCTC CCGGAGCCTG CGCGGGCGTC   360
GCCTGGAAGG GAGAACTTGG GATCGGTGCG GGAACCCCCG CCCTGGCTGG ATCGGCCGAG   420
CGAGCCTGGA AAATGGTAAA TGATCATTTG GATCAATTAC AGGCTTTTAG CTGGCTTGTC   480
TGTCATAATT CATGATTCGG GGCTGGGAAA AAGACCAACA GCCTACGTGC CAAAAAAGGG   540
GCAGAGTTTG ATGGAGTTCG TGGACTTTTC TGTGCGGCTC GCCTCCACAC CTAGAGGATA   600
AGCACTTTTG CAGAGCGCGG TGCGGAGAGA TC ATG TTT GAC TGT ATG GAT GTT    653
                                   Met Phe Asp Cys Met Asp Val
                                    1               5

CTG TCA GTG AGT CCC GGG CAG ATC CTG GAT TTC TAC ACC GCG AGC CCT    701
Leu Ser Val Ser Pro Gly Gln Ile Leu Asp Phe Tyr Thr Ala Ser Pro
         10              15                  20

TCC TCC TGC ATG CTG CAG GAA AAG GCT CTC AAA GCC TGC CTC AGT GGA    749
Ser Ser Cys Met Leu Gln Glu Lys Ala Leu Lys Ala Cys Leu Ser Gly
     25              30              35
                                              ↓Splice Donor Site
TTC ACC CAG GCC GAA TGG CAG CAC CGG CAT ACT GCT CAA TGTAGGTTTA     798
Phe Thr Gln Ala Glu Trp Gln His Arg His Thr Ala Gln (SEQ ID NO: 2)
 40              45              50

TTTTTTTTTT TCCTTTCTTT TACCAAGGAA AAATAAATGT CTCTCTTGCA TGCAATAAAG   858
ACACTGGAAT AAAGTGCAGT GGTGGCAAGA CAAAGGGTTT AA (SEQ ID NO: 1)       900
```

FIG. 1

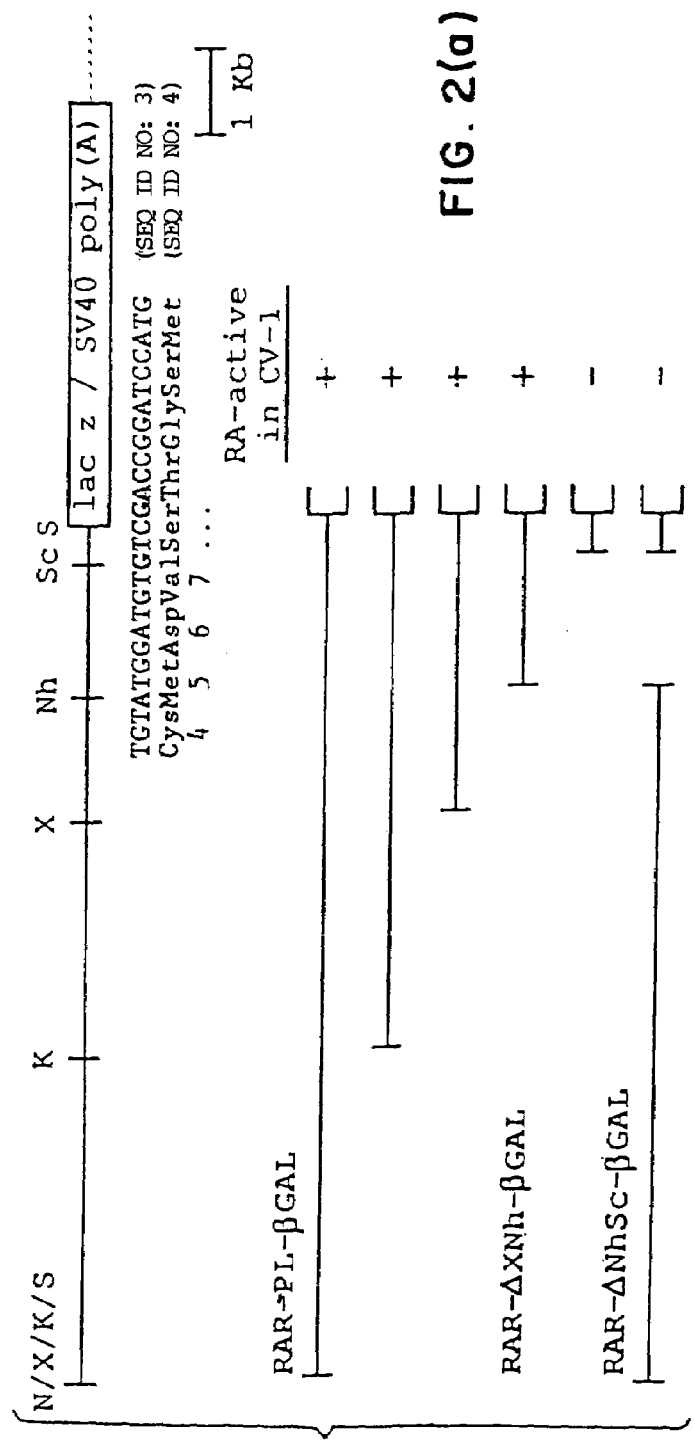

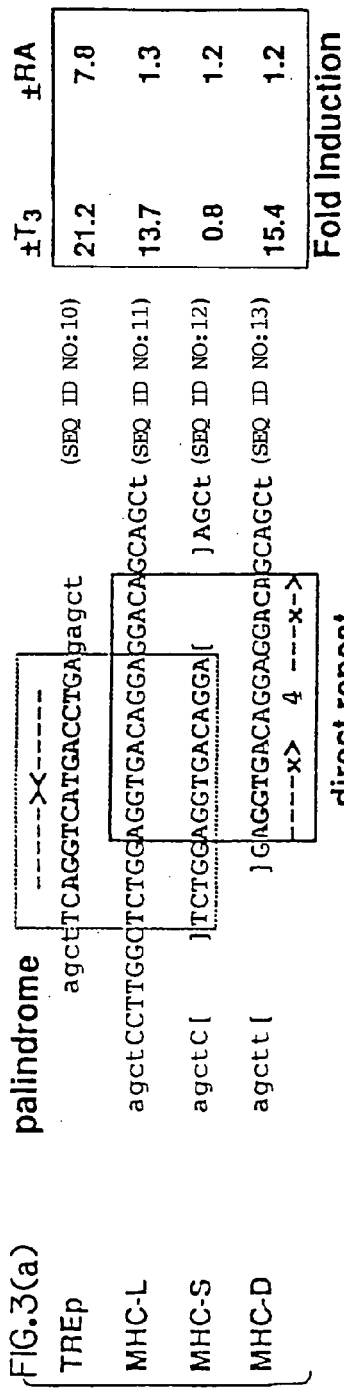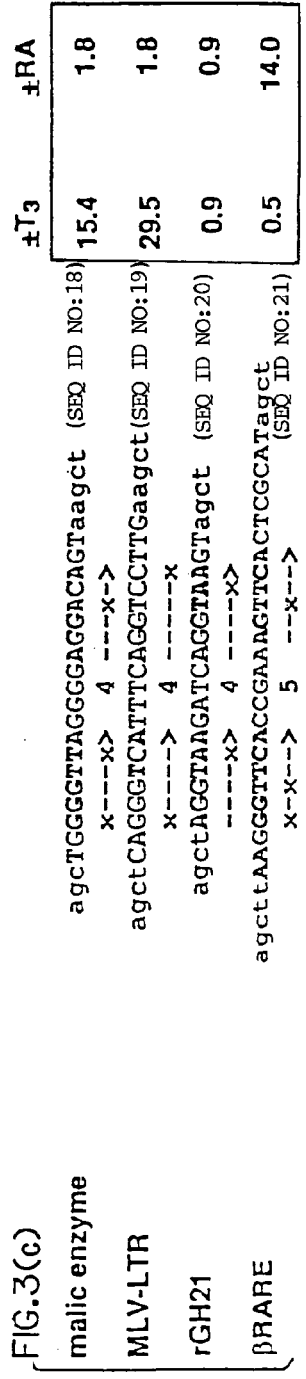

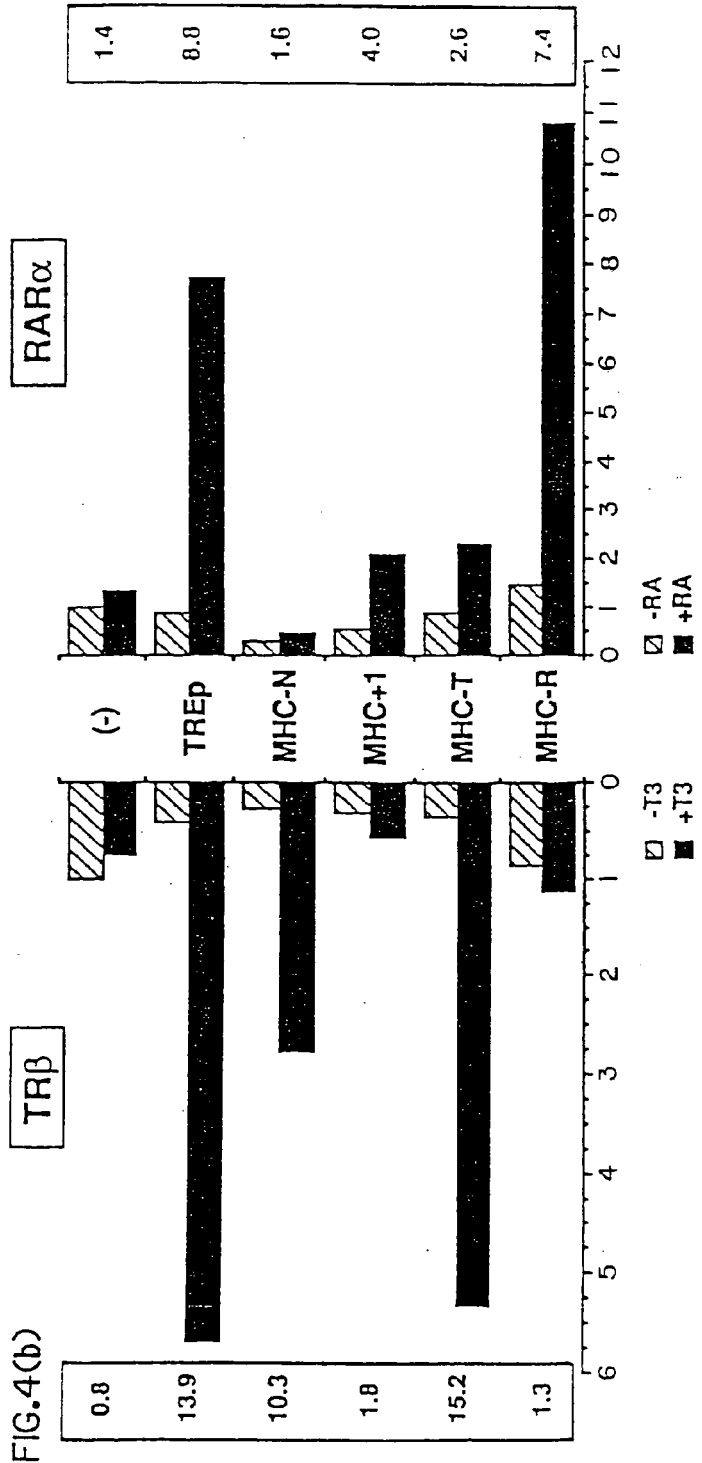

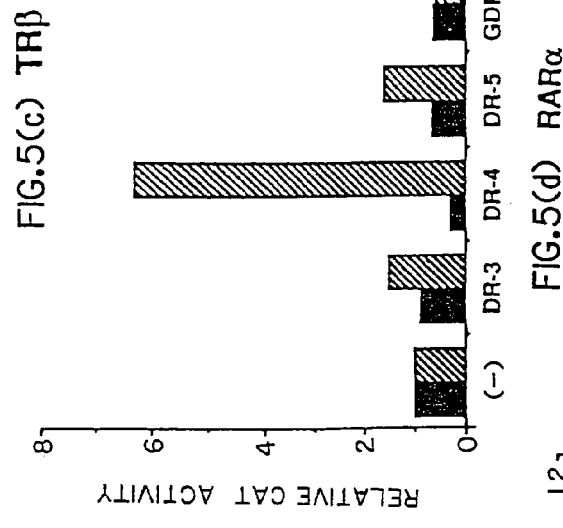
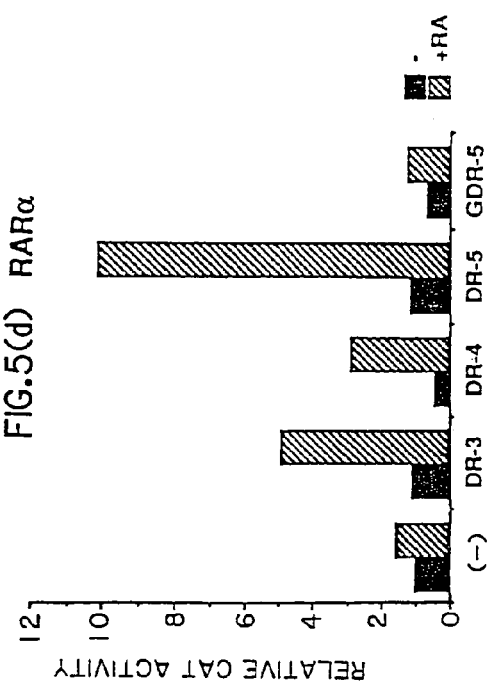
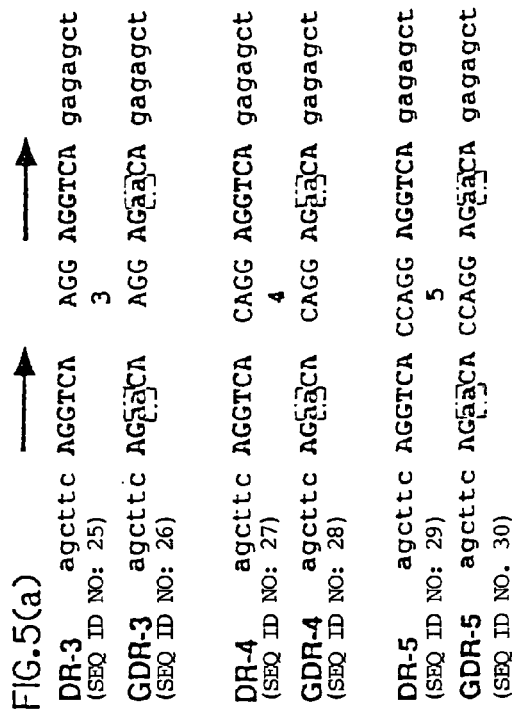
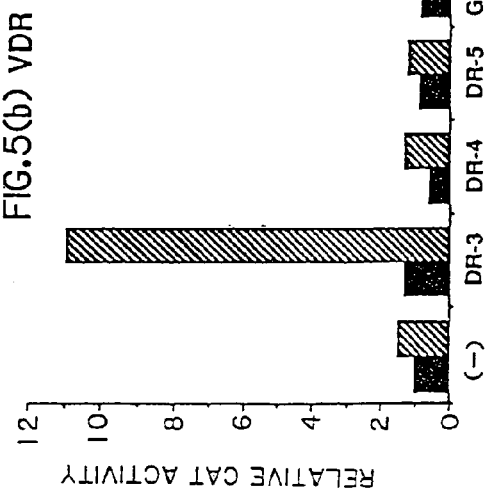
FIG.5(a)
DR-3  agcttc AGGTCA    AGG AGGTCA gagagct
(SEQ ID NO: 25)
GDR-3 agcttc AG̲a̲a̲CA    AGG AG̲a̲a̲CA gagagct
(SEQ ID NO: 26)
DR-4  agcttc AGGTCA   CAGG AGGTCA gagagct
(SEQ ID NO: 27)
GDR-4 agcttc AG̲a̲a̲CA   CAGG AG̲a̲a̲CA gagagct
(SEQ ID NO: 28)
DR-5  agcttc AGGTCA  CCAGG AGGTCA gagagct
(SEQ ID NO: 29)
GDR-5 agcttc AG̲a̲a̲CA  CCAGG AG̲a̲a̲CA gagagct
(SEQ ID NO: 30)
FIG.5(b) VDR
FIG.5(c) TRβ
FIG.5(d) RARα

SEQUENCE LISTING

```
<160> NUMBER OF SEQ ID NOS: 51

<210> SEQ ID NO 1
<211> LENGTH: 900
<212> TYPE: DNA
<213> ORGANISM: Mus sp.
<220> FEATURE:
<221> NAME/KEY: CDS
<222> LOCATION: (633)..(788)
<223> OTHER INFORMATION: Mouse beta-RAR promoter region

<400> SEQUENCE: 1
ccgcggcgct ggctgaaggc tcttgcaggg gtgctgggag tttttaagcg ctgtgagaat      60
cctgggagtt ggtgatgtca gactggttgg gtcatttgaa ggttagcagc ccgggaaggg     120
ttcaccgaaa gttcactcgc atatattagg caattcaatc tttcattccg tgtgacagaa     180
gtggtaggaa gtgagctgct ccgaggcagg agggtctatt ctttgtcaaa ggggggggacc    240 agagttcccg tgcgccgcgg ccacaagact gggatgcaga ggacgcgagc cacccgggca     300
gggagcgtct gggcaccggc ggggtaggac ccgcgcgctc ccggagcctg cgcgggcgtc     360
gcctggaagg gagaacttgg gatcggtgcg ggaaccccg ccctggctgg atcggccgag      420
cgagcctgga aaatggtaaa tgatcatttg gatcaattac aggctttag ctggcttgtc      480 tgtcataatt catgattcgg ggctgggaaa agaccaaca gcctacgtgc caaaaaaggg      540
gcagagtttg atggagttcg tggactttc tgtgcggctc gcctccacac ctagaggata     600
agcatctttg cagagcgcgg tgcggagaga tc atg ttt gac tgt atg gat gtt       653
                                   Met Phe Asp Cys Met Asp Val
                                    1               5 ctg tca gtg agt ccc ggg cag atc ctg gat ttc tac acc gcg agc cct      701
Leu Ser Val Ser Pro Gly Gln Ile Leu Asp Phe Tyr Thr Ala Ser Pro
        10                  15                  20 tcc tcc tgc atg ctg cag gaa aag gct ctc aaa gcc tgc ctc agt gga      749
Ser Ser Cys Met Leu Gln Glu Lys Ala Leu Lys Ala Cys Leu Ser Gly
    25                  30                  35 ttc acc cag gcc gaa tgg cag cac cgg cat act gct caa tgtaggttta       798
Phe Thr Gln Ala Glu Trp Gln His Arg His Thr Ala Gln
40                  45                  50 tttttttttt tcctttcttt taccaaggaa aaataaatgt ctctcttgca tgcaataaag     858
acactggaat aaagtgcagt ggtggcaaga caaagggttt aa                        900

<210> SEQ ID NO 2
<211> LENGTH: 52
<212> TYPE: PRT
<213> ORGANISM: Mus sp.
<220> FEATURE:
<223> OTHER INFORMATION: Mouse beta-RAR promoter region

<400> SEQUENCE: 2

Met Phe Asp Cys Met Asp Val Leu Ser Val Ser Pro Gly Gln Ile Leu
```

```
            1               5                  10                 15
Asp Phe Tyr Thr Ala Ser Pro Ser Ser Cys Met Leu Gln Glu Lys Ala
             20                  25                  30

Leu Lys Ala Cys Leu Ser Gly Phe Thr Gln Ala Glu Trp Gln His Arg
         35                  40                  45

His Thr Ala Gln
     50
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
    Oligonucleotide, Beta-Retinoic Acid Response
    Element
<220> FEATURE:
<221> NAME/KEY: CDS
<222> LOCATION: (1)..(27)

<400> SEQUENCE: 3

```
tgt atg gat gtg tcg acc gga tcc atg                                27
Cys Met Asp Val Ser Thr Gly Ser Met
 1               5
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:
    Amino acid, Beta-Retinoic Acid Response
    Element

<400> SEQUENCE: 4

```
Cys Met Asp Val Ser Thr Gly Ser Met
 1               5
```

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence:
    Oligonucleotide, Beta-Retinoic Acid Response
    Element 1

<400> SEQUENCE: 5
aagcttaagg gttcaccgaa agttcactcg catatattag ctt                    43

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence:
    Oligonucleotide, Beta-Retinoic Acid Response
    Element 2

<400> SEQUENCE: 6
aagcttaagg gttcaccgaa agttcactcg catagctt                          38

<210> SEQ ID NO 7
<211> LENGTH: 34
<212> TYPE: DNA
<213> ORGANISM: Artificial Sequence
<220> FEATURE:

<223> OTHER INFORMATION: Description of Artificial Sequence:
     Oligonucleotide, Beta-Retinoic Acid Response
     Element 3

<400> SEQUENCE: 7
aagcttaagg gttcaccgaa agttcactca gctt                34

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:
     Oligonucleotide, Beta-Retinoic Acid Response
     Element 4

<400> SEQUENCE: 8
aagcttcgaa agttcactcg catagctt                       28

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
     Oligonucleotide, Beta-Retinoic Acid Response
     Element 5

<400> SEQUENCE: 9
aagcttaagg gttcaccgag ctt                            23

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:
     Oligonucleotide, TRE-p

<400> SEQUENCE: 10
agcttcaggt catgacctga gagct                          25

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence:
     Oligonucleotide, MHC-L

<400> SEQUENCE: 11
agctccttgg ctctggaggt gacaggagga cagcagct            38

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
     Oligonucleotide, MHC-S

<400> SEQUENCE: 12
agctctctgg aggtgacagg aagct                          25

<210> SEQ ID NO 13
<211> LENGTH: 28
<212> TYPE: DNA

```
<213> ORGANISM: Artificial Sequence
<220> FEATURE:
<223> OTHER INFORMATION: Description of Artificial Sequence:
      Oligonucleotide, MHC-D

<400> SEQUENCE: 13
agcttgaggt gacaggagga cagcagct                                            28

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide, MHC-N

<400> SEQUENCE: 14
agctggaggt gacaggagga cagcaagct                                           29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide, M1

<400> SEQUENCE: 15
agctggaaat gacaggagga cagcaagct                                           29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide, M2

<400> SEQUENCE: 16
agctggaggt gacgaaagga cagcaagct                                           29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide, M3

<400> SEQUENCE: 17
agctggaggt gacaggaaaa cagcaagct                                           29

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide, malic enzyme

<400> SEQUENCE: 18
agctggggtt aggggaggac agtaagct                                            28

<210> SEQ ID NO 19
<211> LENGTH: 30
<212> TYPE: DNA
<213> ORGANISM: Artificial Sequence
```

```
<220> FEATURE:
<223> OTHER INFORMATION: Description of Artificial Sequence:
      Oligonucleotide, MLV-LTR

<400> SEQUENCE: 19
agctcagggt catttcaggt ccttgaagct                                30

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide, rGH21

<400> SEQUENCE: 20
agctaggtaa gatcaggtaa gtagct                                    26

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide, Beta-RARE

<400> SEQUENCE: 21
agcttaaggg ttcaccgaaa gttcactcgc atagct                         36

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide, MHC+1

<400> SEQUENCE: 22
agctggaggt gaacaggagg acagcaagct                                30

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide, MHC-T

<400> SEQUENCE: 23
agctggaggt gacaggaggt cagcaagct                                 29

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide, MHC-R

<400> SEQUENCE: 24
agctggaggt gaacaggagg tcagcaagct                                30

<210> SEQ ID NO 25
<211> LENGTH: 28
<212> TYPE: DNA
<213> ORGANISM: Artificial Sequence
<220> FEATURE:
```

<223> OTHER INFORMATION: Description of Artificial Sequence:
    Oligonucleotide, DR-3

<400> SEQUENCE: 25
agcttcaggt caaggaggtc agagagct                                                28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:
    Oligonucleotide, GDR-3

<400> SEQUENCE: 26
agcttcagaa caaggagaac agagagct                                                28

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence:
    Oligonucleotide, DR-4

<400> SEQUENCE: 27
agcttcaggt cacaggaggt cagagagct                                               29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:
    Oligonucleotide, GDR-4

<400> SEQUENCE: 28
agcttcagaa cacaggagaa cagagagct                                               29

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence:
    Oligonucleotide, DR-5

<400> SEQUENCE: 29
agcttcaggt caccaggagg tcagagagct                                              30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence:
    Oligonucleotide, GDR-5

<400> SEQUENCE: 30
agcttcagaa caccaggaga acagagagct                                              30

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence:

```
            Substantially pure DNA response element
<220> FEATURE:
<221> NAME/KEY: modified_base
<222> LOCATION: (4)..(5)
<223> OTHER INFORMATION: a, t, c, or g
<220> FEATURE:
<221> NAME/KEY: modified_base
<222> LOCATION: (7)..(21)
<223> OTHER INFORMATION: a, t, c, or g
<220> FEATURE:
<221> NAME/KEY: modified_base
<222> LOCATION: (25)..(26)
<223> OTHER INFORMATION: a, t, c, or g
<220> FEATURE:
<221> NAME/KEY: variation
<222> LOCATION: (7)
<223> OTHER INFORMATION: can be zero or range in length from 2-15
<220> FEATURE:
<221> NAME/KEY: variation
<222> LOCATION: (7)..(27)
<223> OTHER INFORMATION: are at least 1

<400> SEQUENCE: 31
rgbnnmnnnn nnnnnnnnnn nrgbnnm                                          27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence:
      Substantially pure DNA response element
<220> FEATURE:
<221> NAME/KEY: modified_base
<222> LOCATION: (7)..(21)
<223> OTHER INFORMATION: a, t, c, or g
<220> FEATURE:
<221> NAME/KEY: variation
<222> LOCATION: (7)
<223> OTHER INFORMATION: can be zero or range in length from 2-15
<220> FEATURE:
<221> NAME/KEY: variation
<222> LOCATION: (7)..(27)
<223> OTHER INFORMATION: are at least 1

<400> SEQUENCE: 32
aggtcannnn nnnnnnnnnn naggtca                                          27

<210> SEQ ID NO 33
<211> LENGTH: 71
<212> TYPE: PRT
<213> ORGANISM: Artificial Sequence
<220> FEATURE:
<223> OTHER INFORMATION: Description of Artificial Sequence:  Highly
      Conserved Amino Acids of the DNA-Binding Domain of
      Members of the Superfamily
<220> FEATURE:
<221> NAME/KEY: MOD_RES
<222> LOCATION: (2)..(3)
<223> OTHER INFORMATION: any amino acid
<220> FEATURE:
<221> NAME/KEY: MOD_RES
<222> LOCATION: (5)..(6)
<223> OTHER INFORMATION: any amino acid
<220> FEATURE:
<221> NAME/KEY: MOD_RES
<222> LOCATION: (8)
<223> OTHER INFORMATION: any amino acid
<220> FEATURE:
<221> NAME/KEY: MOD_RES
<222> LOCATION: (10)
<223> OTHER INFORMATION: any amino acid
<220> FEATURE:
<221> NAME/KEY: MOD_RES
<222> LOCATION: (12)
```

```
<223> OTHER INFORMATION: any amino acid
<220> FEATURE:
<221> NAME/KEY: MOD_RES
<222> LOCATION: (14)..(17)
<223> OTHER INFORMATION: any amino acid
<220> FEATURE:
<221> NAME/KEY: MOD_RES
<222> LOCATION: (19)..(20)
<223> OTHER INFORMATION: any amino acid
<220> FEATURE:
<221> NAME/KEY: MOD_RES
<222> LOCATION: (23)
<223> OTHER INFORMATION: any amino acid
<220> FEATURE:
<221> NAME/KEY: MOD_RES
<222> LOCATION: (26)
<223> OTHER INFORMATION: any amino acid
<220> FEATURE:
<221> NAME/KEY: MOD_RES
<222> LOCATION: (28)..(38)
<223> OTHER INFORMATION: any amino acid
<220> FEATURE:
<221> NAME/KEY: MOD_RES
<222> LOCATION: (40)..(47)
<223> OTHER INFORMATION: any amino acid
<220> FEATURE:
<221> NAME/KEY: MOD_RES
<222> LOCATION: (49)..(51)
<223> OTHER INFORMATION: any amino acid
<220> FEATURE:
<221> NAME/KEY: MOD_RES
<222> LOCATION: (53)..(54)
<223> OTHER INFORMATION: any amino acid
<220> FEATURE:
<221> NAME/KEY: MOD_RES
<222> LOCATION: (56)..(57)
<223> OTHER INFORMATION: any amino acid
<220> FEATURE:
<221> NAME/KEY: MOD_RES
<222> LOCATION: (59)..(60)
<223> OTHER INFORMATION: any amino acid
<220> FEATURE:
<221> NAME/KEY: MOD_RES
<222> LOCATION: (63)..(64)
<223> OTHER INFORMATION: any amino acid
<220> FEATURE:
<221> NAME/KEY: MOD_RES
<222> LOCATION: (67)..(69)
<223> OTHER INFORMATION: any amino acid

<400> SEQUENCE: 33

Cys Xaa Xaa Cys Xaa Xaa Asp Xaa Ala Xaa Gly Xaa Tyr Xaa Xaa Xaa
  1               5                  10                  15

Xaa Cys Xaa Xaa Cys Lys Xaa Phe Phe Xaa Arg Xaa Xaa Xaa Xaa Xaa
             20                  25                  30

Xaa Xaa Xaa Xaa Xaa Xaa Cys Xaa Xaa Xaa Xaa Xaa Xaa Xaa Xaa Cys
         35                  40                  45

Xaa Xaa Xaa Lys Xaa Xaa Arg Xaa Xaa Cys Xaa Xaa Cys Arg Xaa Xaa
     50                  55                  60

Lys Cys Xaa Xaa Xaa Gly Met
 65                  70

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 34
aggtcaagga ggtca                                              15
```

-continued

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 35
gggtgaatga ggaca                                                    15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 36
gggtgaacgg gggca                                                    15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 37
ggttcacgag gttca                                                    15

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 38
aggtcacagg aggtca                                                   16

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 39
aggtgacagg aggtca                                                   16

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 40
aggtgacagg aggaca                                                   16

```
<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 41
gggttagggg aggaca                                                        16

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 42
gggtcatttc aggtcc                                                        16

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 43
aggtcaccag gaggtca                                                       17

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 44
aggtgaacag gaggtca                                                       17

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 45
ggttcaccga aagttca                                                       17

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 46
aggtcactga cagggca                                                       17
```

```
<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 47
gggtcattca gagttca                                                 17

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 48
taggtagcta g                                                       11

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 49
ctgggtgaat gaggacatta ctgacc                                       26

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 50
aggtcccaga aggtca                                                  16

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide; DNA response element

<400> SEQUENCE: 51
aggtcactag gaggtca                                                 17
```

RESPONSE ELEMENT COMPOSITIONS AND ASSAYS EMPLOYING SAME

RELATED APPLICATIONS

This application is a divisional of application Ser. No. 07/672,530, filed Mar. 19, 1991, now U.S. Pat. No. 6,492, 137, which is a continuation-in-part of application Ser. No. 07/438,757, filed Nov. 16, 1989, now U.S. Pat. No. 5,091, 518, the entire contents of which are hereby incorporated by reference herein.

FIELD OF INVENTION

The present invention relates to the superfamily of nuclear receptors known as the steroid/thyroid hormone receptors and their cognate response elements. More particularly, the present invention relates to the discovery of novel response elements which may be used to control the transcriptional activity of promoters.

BACKGROUND OF THE INVENTION

A central question in eukaryotic molecular biology is how specific DNA-binding proteins bind regulatory sequences to influence cell function and fate. The steroid/thyroid hormone receptors form a superfamily of ligand-dependent transcription factors that are believed to play a part in such cell function and fate. For example, it is known that these receptors transduce extracellular hormonal signals to target genes that contain specific enhancer sequences (referred to as hormone-response elements, or HREs). Each receptor contains a ligand-binding domain and a DNA-binding domain. The receptor undergoes a conformational change when it binds ligand. This conformational change permits the receptor-ligand complex to bind its cognate response element and thereby regulate transcriptional activity of an associated promoter. Transcriptional activation of promoter drives transcription of an operatively associated structural gene.

Sequence comparison and mutational analyses of hormone receptors, such as the glucocorticoid receptor (GR), have identified functional domains responsible for transcriptional activation and repression, nuclear localization, DNA binding, and hormone binding. The DNA binding domain, which is required in order to activate transcription, consists of 66–68 amino acids of which about 20 sites, including nine cysteines ($C_1$ to $C_9$), are invariant among different receptors. The modular structure of members of this receptor superfamily allows the exchange of one domain for another to create functional, chimeric receptors.

The hormone response elements identified thus far are generally structurally related, but they are in fact functionally distinct. The response elements for GR estrogen receptor (ERE)], and thyroid hormone receptor hormone response elements (TREs)] have been characterized in detail; they each consist of a palindromic pair of 'half sites' (Evans, Science 240, 889 (1988); Green and Chambon, Trends in Genetics 4, 309 (1988)]. With optimized pseudo- or consensus response elements, only two nucleotides per half site are different in GRE and ERE [Klock, et al., Nature 329, 734 (1987)]. On the other hand, identical half sites can be seen in ERE and TRE, but their spacing is different [Glass, et al., Cell 54, 313 (1988)]. Moreover, TRE has been shown to mediate transcriptional activation by transfected retinoic acid receptors (RARs) in CV-1 cells whereas non-transfected cells show no response [Umesono et al., Nature 336, 262 (1988)]. In other words, both TR and RAR receptors can activate TREs.

Thus far, however, the response elements for only a few members of the steroid/thyroid superfamily of receptors have been identified. The response elements for many other members of the superfamily, and the relationship between them, if any, remain to be described.

SUMMARY OF THE INVENTION

We have discovered, and characterized by sequence, DNA segments which are response elements operative to confer responsiveness to ligands for several members of the steroid/thyroid superfamily of receptors, for the transcriptional activation and/or repression of promoters in cells. We have also discovered that the transcriptional activity modulating effect of the invention response elements occurs in all mammalian cells in the presence of ligands for several members of the steroid/thyroid superfamily of receptors, indicating that the various hormone receptors recognized by the invention response elements are present endogenously in all of these cells.

Contrary to what has previously been reported in the art for the GRE, ERE and TRE, the novel response elements disclosed herein have a tandem repeat sequence, as opposed to a palindromic sequence which has previously been reported for GRE, ERE and TRE. In addition, the invention response elements are much less susceptible to transcriptional activation by non-cognate receptors than are the previously described response elements (GRE, ERE, TRE).

By using transcriptional control regions comprising response elements of the present invention and a functional promoter, it is now possible to provide recombinant DNA vectors containing a gene, the transcription (and, thereby, also expression) of which is under the control of a promoter, the transcriptional activity of which is responsive to (and modulated by) ligands for several members of the steroid/thyroid superfamily of receptors.

BRIEF DESCRIPTION OF THE FIGURES

FIG. 1 represents the sequence of the mouse βRAR promoter region and the first exon. The TATA and -AGGTCA- motifs are underlined; the first exon splice site is indicated with an arrow.

FIG. 2(a) presents the in vivo analysis of RARβ RA response element sequences, following a series of deletions from the 5'-end of the sequence including the β retinoic acid response element.

FIG. 2 (b) presents sequences of oligonucleotides including the β retinoic acid response element used in the experiments described herein.

FIG. 3 presents the sequence for several hormone response elements and summarizes the responsiveness of such sequences to triiodothyronine ($T_3$) and retinoic acid (RA).

FIG. 4 illustrates the interconversion of the MHC-TRE into an RARE.

FIG. 5 illustrates the selective transactivation of synthetic direct repeat hormone response elements by vitamin $D_3$ ($VD_3$), triiodothyronine ($T_3$), and retinoic acid (RA).

DETAILED DESCRIPTION OF THE INVENTION

In accordance with the present invention, there is provided a substantially pure DNA having the sequence:
5'-RGBNNM-[(N)$_x$-RGBNNM]$_y$-3' (SEQ ID NO:31),
wherein
each R is independently selected from A or G;
each B is independently selected from G, C, or T;

each N is independently selected from A, T, C, or G; and
each M is independently selected from A or C; with the
proviso that at least 4 nucleotides of each -RGBNNM-
group of nucleotides are identical with the nucleotides
at comparable positions of the sequence -AGGTCA-,
x is zero or a whole number falling in the range of 2 up
to 15, and y is at least 1.

Alternatively, the invention response elements can be described as substantially pure DNA having the sequence:

5'-AGGTCA-[(N)$_x$-AGGTCA)$_y$-3' (SEQ ID NO:32),
wherein N, x and y are as defined above, and one or two
of the nucleotides of each -AGGTCA- group of nucleotides can be replaced with a different nucleotide, consistently with the definitions provided above, i.e., the first nucleotide can be replaced with a G; the third nucleotide of the group can be replaced with C or T; the fourth nucleotide of the group can be replaced with A, G, or C; the fifth nucleotide of the group can be replaced with A, G, or T; and the sixth nucleotide of the group can be replaced with C.

In accordance with another embodiment of the present invention, there are provided DNA constructs comprising the above-described response elements operatively linked to a promoter which is not normally subject to transcriptional activation and/or repression by ligands for members of the steroid/thyroid superfamily of receptors; wherein the DNA and the promoter are operatively linked so as to confer transcriptional activation and/or repression activity on said promoter in the presence of a suitable ligand and its associated receptor. The above-described constructs can then be operatively linked to a gene for transcription. The resulting gene-containing DNA construct can then be incorporated into a vector for expression. The resulting vector can then be transformed into suitable host cells.

Cells containing the above-described vectors can then be used for the controlled expression of a gene of interest, in response to the presence or absence of a suitable ligand and its associated receptor.

In accordance with yet another embodiment of the present invention, there is provided a method for testing the activity of a test compound as an agonist of a ligand for a member of the steroid/thyroid superfamily of receptors (to which the invention response elements respond), said method comprising:

(a) culturing a cell (as described above) in the presence of a member of the steroid/thyroid superfamily of receptors, and in the further presence, or in the absence, of the test compound; and thereafter (b) comparing the amount of the protein of interest expressed during the culturing in the presence, or in the absence, of the test compound.

In accordance with still another embodiment of the present invention, there is provided a method for testing the activity of a test compound as an antagonist of a ligand for a member of the steroid/thyroid superfamily of receptors (to which the invention response elements respond), said method comprising:

(a) culturing a cell (as described above) in the presence of a member of the steroid/thyroid superfamily of receptors and a ligand for said receptor to which the response elements of the present invention respond, and further:
(i) in the presence of the test compound, or
(ii) in the absence of the test compound; and thereafter
(b) comparing the amount of the protein of interest expressed during the (i) and (ii) culturing steps.

In accordance with a further embodiment of the present invention, there is provided a method to distinguish whether or not responsiveness to a ligand for a first member of the steroid/thyroid superfamily of receptors occurs via a pathway unique to at least one member of the steroid/thyroid superfamily, relative to other member(s) of the steroid/thyroid superfamily, said method comprising:

contacting a vector containing an invention response element (as described above) with a ligand for said first member of the steroid/thyroid superfamily of receptors, and varying ratios of expression vectors for a first and second receptor, and thereafter determining the effect of increasing ratios of the first receptor expression vector to the second receptor expression vector on transcription activation and/or repression of said response element by said ligand for said first member of the steroid/thyroid superfamily of receptors.

In accordance with another aspect of the present invention, there is provided a method to screen compounds to identify those compounds which act as ligands for members of the steroid/thyroid superfamily of receptors, said method comprising:

contacting said compound with cells (as described above), wherein said cells are further transfected with an expression vector for said member of the steroid/thyroid superfamily of receptors, wherein said receptor, in the presence of its cognate ligand, is capable of binding to response elements of the present invention, and thereafter assaying for the modulation of expression of the reporter protein.

In the present specification and claims, reference is made to phrases and terms of art which are expressly defined for use herein as follows:

"RAβ" or "βRAR" both refer to retinoic acid receptor beta;

"VDRE" means vitamin D3 response element;

"TRE" means thyroid hormone response element;

"T$_3$" means triiodothyronine;

"CAT" means chloramphenicol acetyl transferase;

"LUC" means firefly luciferase;

"β-Gal" means β-galactosidase;

"COS" means monkey kidney cells which express T antigen (Tag) [see, for example, Gluzman in Cell, 23: 175 (1981)];

"CV-1" means mouse kidney cells from the cell line referred to as "CV-1". CV-1 is the parental line of COS. Unlike COS cells, which have been transformed to express SV40 T antigen (Tag), CV-1 cells do not express T antigen;

"transcriptional control region" or "transcriptional control element" refer to a DNA segment comprising a response element operatively linked to a promoter to confer ligand responsiveness to transcriptional activity of the promoter;

"operatively linked" means that the linkage (i.e., DNA segment) between the DNA segments so linked is such that the described effect of one of the linked segments on the other is capable of occurring. Effecting operable linkages for the various purposes stated herein is well within the skill of those of ordinary skill in the art, particularly with the teaching of the instant specification;

"promoter being naturally unresponsive to ligand" means that ligand does not enhance transcription from the promoter to an observable extent in a cell (e.g., a mammalian cell) unless a response element of the invention is spliced or inserted (upstream of the promoter) relative to the direction of transcription therefrom, by recombinant DNA or genetic engineering methods, into a DNA segment comprising the promoter, and linked to the promoter in a manner which makes transcriptional activity from the promoter operatively responsive to ligand;

"substantial sequence homology" refers to DNA or RNA sequences which have de minimus sequence variations from, and retain the same functions as, the actual sequences disclosed and claimed herein;

"members of the steroid/thyroid superfamily of receptors" refers to hormone binding proteins that operate as ligand-dependent transcription factors, including identified members of the steroid/thyroid superfamily of receptors for which specific ligands have not yet been identified (referred to hereinafter as "orphan receptors"). Each such protein has the intrinsic ability to bind to a specific DNA sequence in a target gene. Following binding, the transcriptional activity of the gene is modulated by the presence or absence of the cognate hormone (ligand). The DNA-binding domains of all of these nuclear receptors are related, consisting of 66–68 amino acid residues, and possessing about 20 invariant amino acid residues, including nine cysteines. A member of the superfamily can be identified as a protein which contains these diagnostic amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153). The highly conserved amino acids of the DNA-binding domain of members of the superfamily are as follows:

Cys-X-X-Cys-X-X-Asp*-X-Ala*-X-Gly*-X-Tyr*-X-X-X-X-Cys-X-X-Cys-Lys*-X-Phe-Phe-X-Arg*-X-X-X-X-X-X-X-X-(X-X-)Cys-X-X-X-X-X-(X-X-X-)Cys-X-X-X-Lys-X-X-Arg-X-X-Cys-X-X-Cys-Arg*-X-X-Lys*-Cys-X-X-X-Gly*-Met (SEQ ID NO:33);

wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues). Examplary members of the steroid/thyroid superfamily of receptors include steroid receptors such as glucocorticoid receptor, mineralocorticoid receptor, progesterone receptor, androgen receptor, vitamin $D_3$ receptor, and the like; plus retinoid receptors, such as RARα, RARβ, RAR$_γ$, and the like; thyroid receptors, such as TRα, TRβ, and the like; as well as other gene products which, by their structure and properties, are considered to be members of the superfamily, as defined hereinabove. Examples of orphan receptors include HNF4 [see, for example, Sladek et al., in Genes & Development 4: 2353–2365 (1990)], the COUP family of receptors [see, for example, Miyajima et al., in Nucleic Acids Research 16: 11057–11074 (1988), Wang et al., in Nature 340: 163–166 (1989)], COUP-like receptors and COUP homologs, such as those described by Mlodzik et al., in Cell 60: 211–224 (1990) and Ladias et al., in Science 251: 561–565 (1991), the ultraspiracle receptor [see, for example, Oro et al., in Nature 347: 298–301 (1990)], and the like;

"suitable ligands" for hormone receptors of the steroid/thyroid superfamily refers to the specific ligand(s) which, in combination with its cognate receptor, is effective to transcriptionally activate the response element to which the cognate receptor binds (i.e., RA/RAR/RARE, vitamin $D_3$/vitamin $D_3$ receptor/VDRE, $T_3$/TR/TRE, estrogen/ER/ERE, and the like).

The nucleotides which occur in the various nucleotide sequences appearing herein have their usual single-letter designations (A, G, T, C or U) used routinely in the art.

In the present specification and claims, references to Greek letters may either be written out as alpha, beta, etc. or the corresponding Greek letter symbols (e-g., α, β, etc.) may sometimes be used.

The response elements of the present invention can be composed of two or more "half sites", wherein each half site comprises the sequence -RGBNNM-, with the proviso that at least 4 of the nucleotides in the half-site sequence are identical with the nucleotides at comparable positions of the sequence -AGGTCA-. Where one of the half sites varies by 2 nucleotides from the preferred sequence of -AGGTCA-, it is preferred that the other half site of the response element be the same as, or vary from the preferred sequence by no more than 1 nucleotide. It is presently preferred that the 3'-half site (or downstream half site) of a pair of half sites vary from the preferred sequence by at most 1 nucleotide.

Exemplary response elements contemplated by the present invention are derived from various combinations of half sites having sequences selected from, for example, -AGGTCA-, -GGTTCA-, -GGGTTA-, -GGGTGA-, -AGGTGA-, -GGGTCA-, and the like.

The spacer nucleotide sequence employed in the invention response elements can be any combination of C, T, G, or A.

Exemplary response elements contemplated by the present invention include:
5'-AGGTCA-AGG-AGGTCA-3' (SEQ ID NO:34),
5'-GGGTGA-ATG-AGGACA-3' (SEQ ID NO:35),
5'-GGGTGA-ACG-GGGGCA-3' (SEQ ID NO:36),
5'-GGTTCA-CGA-GGTTCA-3' (SEQ ID NO:37),
5'-AGGTCA-CAGG-AGGTCA-3' (SEQ ID NO:38),
5'-AGGTGA-CAGG-AGGTCA-3' (SEQ ID NO:39),
5'-AGGTGA-CAGG-AGGACA-3' (SEQ ID NO:40),
5'-GGGTTA-GGGG-AGGACA-3' (SEQ ID NO:41),
5'-GGGTCA-TTTC-AGGTCC-3' (SEQ ID NO:42),
5'-AGGTCA-CCAGG-AGGTCA-3' (SEQ ID NO:43),
5'-AGGTGA-ACAGG-AGGTCA-3' (SEQ ID NO:44),
5'-GGTTCA-CCGAA-AGTTCA-3' (SEQ ID NO:45),
5'-AGGTCA-CTGAC-AGGGCA-3' (SEQ ID NO:46),
5'-GGGTCA-TTCAG-AGTTCA-3' (SEQ ID NO:47),
5'-AAGCTTAAG-GGTTCA-CCGAA-AGTTCA-CTCAGCTT-3' (SEQ ID NO:7),
5'-AAGCTTAAG-GGTTCA-CCGAA-AGTTCA-CTCGCATAGCTT-3' (SEQ ID NO:6),
5'-AAGCTTAAG-GGTTCA-CCGAA-AGTTCA-CTCGCATATATTAGCTT-3' (SEQ ID NO:5), and the like.

Presently preferred response elements contemplated by the present invention include:
5'-AGGTCA-AGG-AGGTCA-3' (SEQ ID NO:34),
5'-AGGTCA-CAGG-AGGTCA-3' (SEQ ID NO:38),
5'-AGGTGA-CAGG-AGGTCA-3' (SEQ ID NO:39),
5'-AGGTCA-CCAGG-AGGTCA-3' (SEQ ID NO:40),
5'-AGGTGA-ACAGG-AGGTCA-3' (SEQ ID NO:44),
and the like. These are especially preferred because they represent synthetic sequences which have not been observed in nature, and thus are applicable to a wide variety of reporter systems i.e., the use of these response elements will not be limited due to any species preference based on the source of the sequence).

With respect to the promoter which is part of a transcriptional control region of the invention, practically any promoter may be used, so long as the transcriptional activity of such a promoter can be modulated by a response element of the present invention (when suitably positioned upstream from the promoter). Among such promoters are Delta-MTV promoter of mouse mammary tumor virus, Herpes simplex thymidine kinase (tk) promoter, basal Simian virus SV-40 promoter, the Drosophila alcohol dehydrogenase (ADH) promoter, and the like. Presently preferred are promoters which require a response element for activity.

Virtually any protein or polypeptide of interest can be made with cells transformed with an expression vector of the invention. Such proteins include hormones, lymphokines, receptors or receptor subunits, immunoglobulin chains and the like. Indicator proteins such as LUC, CAT, and β-Gal can also be made.

Among the types of cells that can be transformed in accordance with the invention are mammalian cells, avian cells, insect cells, and the like, such as, for example, CV-1, COS, F9, P19, CHO, HeLa, NIH 3T3, HuTu80, Rat2 fibroblasts, HT1080.T, chick embryo fibroblasts, quail QT6, Drosophila Schneider 52 cells, and the like.

The invention method for determining the activity of a test compound as an agonist or antagonist of ligands for members of the steroid/thyroid superfamily of receptors can be carried out employing standard assay techniques, as are well known by those of skill in the art. See, for example, Mangelsdorf et al., in Nature 345: 224–229 (1990).

Test compounds contemplated for screening in accordance with the invention assay methods include any compound which can potentially affect the ability of receptor to modulate transcription activity through a response element of the present invention.

In accordance with a specific embodiment of the present invention, wherein it is possible to distinguish whether or not responsiveness to a ligand for a first member of the steroid/thyroid superfamily of receptors occurs via a pathway unique to a first receptor (relative to other member(s) of the superfamily) or via some other pathway, responsiveness to said ligand via the pathway for the first receptor would result in increased amounts of transactivation as a function of increased expression of said first receptor, while responsiveness to said ligand via the pathway for the second receptor would result in reduced levels of transactivation as a function of increased expression of said second receptor (caused by competition by the second receptor for ligand needed for the activation of the first receptor).

Receptors, assay methods, and other subject matter pertinent to the subject matter of the present specification may be found in the following references, which are incorporated herein by reference: Commonly assigned U.S. patent application Ser. No. 108,471, filed Oct. 20, 1987 and published as PCT International Publication No. WO 88,03168; commonly assigned U.S. patent application Ser. No. 276,536, filed Nov. 30, 1988 and published as European Patent Application Publication No. 0 325 849; commonly assigned U.S. patent application Ser. No. 370,407, filed Jun. 22, 1989, said Application listing a Budapest Treaty Deposit of a plasmid harboring a cDNA encoding a gamma-retinoic acid receptor, said deposit having been made Jun. 22, 1989 and bearing American Type Culture Collection Accession No. 40623; Zelent et al., Nature 339, 714 (1989); Petkovich et al., Nature 330, 444 (1987); Brand et al., Nature 332, 850 (1988).

Because the DNA segments which comprise the response elements of the present invention are relatively short, they may be provided synthetically, that is by synthesizing the response element-containing oligonucleotide on a DNA synthesizer as is known in the art. It is frequently very desirable to provide restriction endonuclease sites at the 3'- and 5'-ends of the oligomer, such that the synthetic response element may be conveniently inserted into a DNA expression vector at a site upstream from the promoter, whose transcriptional activity is to be enhanced and which drives transcription of the desired gene. As those of ordinary skill in the art will understand, the response elements of the present invention, like other response elements, are orientation and, with wide latitude, position independent. Thus, the response elements of the present invention are functional in either orientation and may be placed in any convenient location from about 30 nucleotides upstream to about 10,000 nucleotides upstream from the promoter to be affected.

Preferred cells for use with expression systems employing transcriptional control regions comprising invention response element are mammalian cells such as COS cells and CV-1 cells. COS-1 (referred to as COS) cells are mouse kidney cells that express SV40 T antigen (Tag); while CV-1 cells do not express SV40 Tag. CV-1 cells are convenient because they lack any endogenous glucocorticoid or mineralocorticoid or other known members of the steroid/thyroid superfamily of hormone receptors, except that they do produce low levels of βRAR. Thus, via gene transfer with appropriate expression vectors comprising a heterologous gene under the control of a transcriptional control region of the invention, it is possible to convert these host cells into transformed cells which produce increased quantities of a desired protein in response to induction by a ligand for a member of the steroid/thyroid superfamily of receptors.

Expression plasmids containing the SV40 origin of replication can propagate to high copy number in any host cell which expresses SV40 Tag. Thus, expression plasmids carrying the SV40 origin of replication can replicate in COS cells, but not in CV-1 cells. Although increased expression afforded by high copy number is desirable, it is not critical to the assay systems described herein. The use of any particular cell line as a host is also not critical, although CV-1 cells are presently preferred because they are particularly convenient.

The invention will now be described in detail by reference to the following non-limiting examples.

EXAMPLES

Example 1

The following demonstrates that the sequences in the promoter of the mouse RARβ gene confer retinoic acid (RA) responsiveness, and that these sequences represent a target specific for the three RA receptor subclasses (i.e., alpha-, beta-, and gamma-RAR). The RA response element (RARE) does not mediate significant transcriptional activation by estrogen or glucocorticoid, but it does weakly mediate (by about one order of magnitude less) the transcriptional activation by vitamin D receptor or thyroid hormone receptors (complexed with cognate ligands).

A mouse liver genomic DNA library (Clonetech) in lambda vector EMBL3 was screened with the BamHI-SphI fragment of the human RARβ cDNA clone B1-RARe [see Benbrook et al., in Nature 333: 669–672 (1988)] to localize the RARE in the gene. The probe used contains only first exon sequences, which are unique to the βRAR gene. A clone harboring a 20 kb insert was isolated (containing approximately 10 kb of upstream sequence, the complete first exon, and 10 kb of the first intron), and the region surrounding the first exon was subcloned and subjected to dideoxy sequence analysis. The sequence of the portion of this clone containing the first exon and proximal 5' DNA is shown in FIG. 1, which represents the sequence of the mouse βRAR promoter region and the first exon. The TATA and -AGGTCA- motifs are underlined; the first exon splice site is indicated with an arrow.

The 10 kb upstream region of the genomic fragment isolated as described above was fused in-frame just downstream of the RARβ translation initiation codon to a β-galactosidase reporter gene (see FIG. 2a, which presents the in vivo analysis of RARβ RA response element sequences, following a series of deletions from the 5'-end of the sequence including the β retinoic acid response element. The sequence at the junction between the mouse RARβ gene and the β-galactosidase reporter gene is as shown. Numbered amino acids correspond to the native RAREβ translation product. Restriction sites are abbreviated as follows: N=NotI, X=XhoI, K=KpnI, S=SalI, Nh=NheI, Sc=SacII. The dotted line represents plasmid sequences).

RAR-PL-βGAL was introduced into monkey kidney CV-1 cells cotransfected with RAR expression vector. Enzyme activity was induced upon retinoic acid addition, indicating that this region of genomic DNA contains a functional promoter which is responsive to—retinoic acid. This was accomplished by introducing a SalI restriction site into the genomic clone at the indicated position by site-directed mutagenesis; the 10 kb genomic fragment was then excised and cloned into the β-galactosidase vector pLSV [a derivative of pGH101; Herman et al., Nucleic Acids Research 14:7130 (1986)], modified to contain a SalI site and a polylinker sequence by oligo addition, to yield RAR-PL-βGAL.

A series of deletions from the 5'-end of RAR-PL-βGAL reveal that sequences mediating RA induction reside within the 2 kb NheI-SacII fragment (see FIG. 2a and the Table below). Subfragments of this region were cloned into the enhancer-dependent luciferase reporter plasmid DMTV-LUC, which contains the mouse mammary tumor virus promoter with the natural GR response elements deleted [see Hollenberg et al., in Cell 55: 899–906 (1988). A 183 bp SmaI fragment (see FIG. 1) is able to confer retinoic acid responsiveness to this heterologous promoter in either orientation (see data presented in the Table below). Oligonucleotide sequences derived from this region (see FIG. 2b) were then used to further define the RA response element, either in DMTV-LUC or DMTV-CAT (see data presented in the Table below). FIG. 2(b) presents sequences of oligonucleotides including the β retinoic acid response element used in these experiments. The terminal lower case bases are foreign to the RARβ promoter, and were included to allow insertion into the unique HindIII site of the Delta-MTV vector.

Thyroid hormone response element (TRE) has been shown to mediate transcriptional activation by transfected RARs in CV-1 cells, whereas non-transfected cells show no response [see Umesono et al., in Nature 336: 262–265 (1988)]. Surprisingly, Delta-MTV-CAT—constructs βRE1, βRE2, and βRE3 see FIG. 2) showed robust RA-dependent induction in the—absence of cotransfected RAR expression vector. Cotransfection of RAR-alpha expression vector increased induction by only two-fold, which demonstrates that CV-1 cells express a low level of endogenous RA receptor that is sufficient for efficient activation of vectors containing the βRE, but apparently below a threshold for activation of the previously studied TREs. A survey of the following cell lines indicated that all were able to efficiently transactivate the βRARE in an RA-dependent fashion in the absence of transfected RAR expression vector: CV-1, F9 and PI9 (mouse teratocarcinomas), CHO, HeLa, NIH 3T3, Rat2 fibroblasts, HT1080.T (human lymphoid), chick embryo fibroblasts, and quail QT6 cells. No cell line has yet been tested which does not express this activity.

Inspection of the sequences of βRE1, βRE2, and βRE3 (see FIG. 2b) identifies a tandem repeat of the 6 bp motif. The center to center separation of 11 bp between these repeats is one turn of the DNA helix. Constructs containing single copies of either the 5'- or 3'-half site (βRE4 and βRE5) are functional only upon cotransfection of RAR expression vectors (see FIG. 2d). Not only does this indicate that the RARE is a bonafide target of all three RAR subtypes expressed from cloned cDNA, but it also demonstrates that these half sites can serve as a minimal RA response element in the context of the Delta-MTV promoter. Apparently, a single half site element of the RARβ gene would reciprocally be responsive to the TR, ER, and/or other members of the receptor superfamily. Cotransfection of the ER, GR, in CV-1 cells with construct βRE1 failed to result in appreciable activation in the absence or following addition of the appropriate ligand, although cotransfection with TR and vitamin D receptor (VD3R) CV-1 cells with construct βRE1 did weakly (about 10- to 20-fold less) activate their cognate response elements.

Five µg of each of the constructs indicated in the Table were transfected into CV-1 cells with either RSV-LUC or RSV-βGAL to normalize transfection efficiencies. Transfections also included RARα expression vector. Each value in the Table represents duplicate measurements of plates treated with $10^{-7}$M RA (βGAL experiments) or $10^{-6}$M RA (luciferase experiments) relative to plates treated with solvent only. The 183 SmaI restriction fragment (shown in FIG. 1) was inserted either in the forward (F) or reverse (R) orientation relative to the Delta-MTV promoter. The (NR) construct contains a 45 bp oligo sequence located 24 bp 3' of βRE1 in the RARβ promoter which was nonresponsive to RA.

Plasmids were transfected into CV-1 cells and assayed for β-galactosidase activity either without or with the addition of $10^{-7}$M RA. Negative responses were two-fold induction or less; positive inductions were seven-fold or greater.

Cells were transfected in 10 cm dishes with 10 µg of DNA containing 5 µg of reporter plasmid, 1–2 µg of either RSV-LUC (a), or RSV-βGAL or pCH110 (c and d), pGEM4 as carrier DNA, and for the experiments shown in a and d, 1 µg of RSV-RAR expression vector or the same amount of an RSV vector generating a nonsense transcript. Cells were harvested 1 day after addition of retinoic acid. All CAT assays represent equivalent amounts of β-galactosidase activity; β-GAL assays were normalized to luciferase activity.

TABLE

Retinoic acid inducibility of reporter constructs

| Construct | Fold increase |
| --- | --- |
| RAR-PL-βGAL | 14 |
| RAR-DXN-βGAL | 22 |

TABLE-continued

Retinoic acid inducibility of reporter constructs

| Construct | Fold increase |
|---|---|
| RAR-DNhSc-βGAL | 2 |
| DMTV-LUC | 2 |
| DMTV-Sma183F-LUC | 10 |
| DMTV-Sma183R-LUC | 9 |
| DMTV-LUC | 2 |
| DMTV-(NR)-LUC | 2 |
| DMTV-βRE1-LUC | 14 |

Example 2

Receptor expression plasmids used in the following cotransfection assays have been described previously (pRShTRβ [see Thompson, et al., Proc. Natl. Acad. Sci. U.S.A. 86: 3494–3498 (1989)]; pRShRARα [see Giguere, et al., Nature 330: 624–629 (1987)]; pRShRARβ and pRshRARγ [see Ishikawa, et al., Mol. Endocrinol, 4: 837–844 (1990)]; and pRShVDR, [Schule, et al., Cell 61: 497–504 (1990)]. A basal reporter plasmid ΔSV-CAT was constructed by replacing the TK promoter in TK-CAT [Damm, et al., Nature 339: 593–597 (1989)] with the SphI-HindIII fragment of the SV40 early promoter. All of the recombinant CAT reporter plasmids used herein harbor a single copy of the indicated oligonucleotides at the unique HindIII site upstream of the SV40 promoter. Identity of the inserted oligonucleotides was confirmed by sequencing. To improve production of receptor proteins in COS cells, a new eukaryotic expression vector pCMX was prepared by modifying the plasmid CDM8 [Seed, B., Nature 329: 840–842 (1987)]. The CDM8 was cut with MluI and StuI in order to release the DNA fragment encoding the CMV/T7 promoter, SV40 small t intron/poly A signal, polyoma virus enhancer/origin, and SV40 enhancer/origin. The resulting fragment was ligated to a larger fragment of PvuII-digested PUC 19. An internal deletion was introduced between unique BamHI and BclI sites present in the −8 portion. The stuffer sequence flanked by XbaI sites was replaced with a synthetic polylinker coding for 5'-KpnI/Asp718-EcoRV-BamHI-MscI-NheI-3', followed by a stretch of 5'-<u>TAGGTAGC TAG</u>-3' (SEQ ID NO:48) which can function as a universal termination signal for protein translation. The coding sequence of the luciferase [de Wet, et al., Mol. Cell. Biol. 7: 725–737 (1987)] and human TRβ, RARα, and VDR was placed in the polylinker region of the pCMX, generating pCMX-LUC, pCMX-hTRβ, pCMX-hRARα, and pm-hVDR, respectively. The translation start site of the RARα was modified to ACCACC<u>ATG</u> by attaching the synthetic linker encoding a consensus translation start signal [Hollenberg, et al., Cell 55: 899–906 (1988)]. This modification resulted in much better yield of the receptor translation as judged in the in vitro-reticulocyte lysate translation system.

For cotransfection assays, a monkey kidney cell line CV-1 was kept in Dulbecco's modified Eagle's medium (DMEM) supplemented with 10% charcoal-resin double split calf bovine serum. Transfections were performed via calcium-phosphate precipitation method as described by Umesono, et al. in Cell 57: 1139–1146 (1989), with 0.5 μg of a pRS receptor expression plasmid, 1.0 μg of a reporter CAT plasmid, 5 μq of pRAS-βGAL [Umesono, et al., Cell 57: 1139–1146 (1989)] as an internal control, and 8.5 μg of carrier plasmid pUC19. The cells were transfected for 8 hours; after washing the DNA precipitates, the cells were then incubated for an additional 36 hours with or without the ligand ($T_3$, 100 nM; RA, 1 μM; 1,25-(OH)$_2$ vitamin $D_3$, 100 nM). Cell extracts were prepared for βGAL and CAT assays, as described by Umesono, et al., supra. Transfection of F9 teratocarcinoma cells was carried out employing a similar method except the cells were incubated for 12 hours in the presence of the DNA precipitates, and the RA was added at 1 μM for another 24 hours before harvesting the cells. 2, 5, and 4 μg of the reporter, pRAS-βGAL, and pUC19 were used, respectively.

For DNA binding assays, COS cells were cultured in DMEM with 10% calf bovine serum and transfected by the calcium phosphate method with 20 μg of the pCMX receptor expression plasmid for 6 hours followed by a glycerol shock. After incubating the transfected COS cells for another 48 hours, the cells were harvested to prepare extracts for the DNA binding assay, carried out as described by Damm et al., Nature 339: 593–597 (1989). The extracts were made in 20 mM HEPES (pH 7.4), 0.4 M KCl, 2 mM DTT and 20% glycerol. A similar method was employed to prepare a whole cell extract from F9 stem cells. For the binding, 5 μg (COS) or 10 μg (F9) of proteins was incubated on ice for 20 minutes, first in 20 mM HEPES, 80 mM KCl, 1 mM DTT, 0.1% NP40, 2.5/g of poly dI/dC, and 10% glycerol (cold competitor oligonucleotides, when included, were added during this pre-incubation period). Then 40 fmole of $^{32}$P-labeled oligonucleotide probe (1–2×10$^5$ cpm, prepared by filling-in reaction using Klenow polymerase in the presence of α-$^{32}$P-DCTP) was added to the reaction mixture, followed by incubation at room temperature for 30 minutes. The receptor-DNA complexes were resolved by electrophoresis through 5% polyacrylamide gel containing 5% glycerol at 6 V/cm at room temperature. Under the conditions employed, inclusion of the ligand did not alter the DNA binding pattern of the receptor proteins.

It has previously been shown that a palindromic TRE (TREp) mediates both $T_3$ and retinoic acid response, suggesting that the TR and RAR may regulate overlapping sets of genes [Umesono, et al., Nature 336: 262–265 (1988)]. To test whether coregulation is a general feature of TREs, the properties of the $T^3$-sensitive MHC gene promoter were examined. Accordingly, a reporter plasmid covering a 168 bp segment of the MHC α gene promoter [αTRE-CAT; Izumo, et al., Nature 334: 539–542 (1988)] was cotransfected into CV-1 cells together with expression plasmids for the human RAR α, β, or γ [Giguere, et al., Nature 330: 624–629 (1987); Ishikawa, et al., Mol. Endocrinol 4: 837–844 (1990)] or the human TRβ [Thompson, et al., Proc. Natl. Acad. Sci. U.S.A. 86: 3494–3498 (1989)]. In the absence of the receptor expression plasmids, no stimulation of the CAT enzyme activity was observed by RA or $T_3$. Expression of TRβ, however, conferred a significant $T_3$ response consistent with previous result employing the rat TRα (Izumo, et al., supra). On the other hand, production of any one of three isoforms of the RARs failed to promote an RA response although similar CAT reporter constructs encoding TREp are responsive to both TRs and RARs.

To understand the molecular basis of this phenotypic difference between the TREp and the MHC-TRE, a set of CAT reporters based on a minimal SV40 early promoter (ΔSV-CAT) was prepared. Co-transfection experiments with the TRβ expression vector demonstrated that promoters harboring either the TREp or the wild-type MHC sequence (MHC-L) are responsive to $T_3$ (see FIG. 3a).

Target hormone response elements described in FIG. 3 were synthesized as double-stranded oligonucleotides with an overhanging tetranucleotide (5'-agct-3') at both ends. A single copy of these oligonucleotides was cloned at the unique HindIII site present in the basal promoter CAT construct ΔSV-CAT. Capitalized portions in the nucleotide sequences correspond to those found in the natural promoters except TREp and rGH21, which are synthetic. Bold letters indicate the "AGGTCA" motif and "X" denotes a nucleotide substitution from this motif. Numbers between the arrows are the size of the spacer and those in columns represent the fold inductions of the CAT enzyme activity stimulated by the hormones in either the TRβ (±T$_3$ at 100 nM) or RARα (±RA at 1 μM) producing CV-1 cells. Inductions observed on the basal construct ΔSV-CAT by T$_3$ and RA are 0.8 and 1.4 fold, respectively.

In FIG. 3a, the TREp referred to is an optimized palindromic rat growth hormone TRE (see Glass et al., supra) which stands also as an efficient RARE (see Umesono et al., supra). MHC-L encodes a TRE localized at positions –XXX and –YYY in the MHC gene promoter (see Glass et al., supra). MHC-S and MHC-D contain deletion(s), indicated by brackets, from the MHC-L.

Because the MHC-L resembles the rat growth hormone TRE and TREp, it has been proposed that the actual response element is composed of a partial palindrome of AGGTCA [see FIG. 3a; see also Izumo, et al., supra, and Glass, et al., Cell 59: 697–708 (1989)]. However, a restricted region corresponding to the predicted palindrome (MHC-S reporter) failed to confer T$_3$ responsiveness, indicating that this proposal is incorrect. In contrast, a segment of the MHC sequence (MHC-D) including an adjacent sequence, resulted in a recovery of the full response, delineating a minimal boundary for the MHC-TRE. An examination of this sequence surprisingly fails to reveal a palindrome, but instead identifies a direct (i.e., tandem) repeat of the hexamers AGGTGA and AGGACA.

While each individual half-site resembles the AGGTCA motif in TREp, the orientation of the half sites in the MHC-TRE is distinct. The intriguing ability of this element to respond to T$_3$ and its failure to respond to RA suggested that detailed exploration of the properties of the sequence might reveal additional detail about hormone response. As shown in FIG. 3b, MHC-N encodes a 23-nucleotide core of the wild-type sequence (MHC-TRE). M1 and M3 contain specific nucleotide substitutions in the proposed direct repeat motif (denoted by shadowed letters and "X" in the arrow), while M2 mutant instead carries specific nucleotide substitutions in the presumed palindrome. Using COS cell extracts prepared in the presence or absence of the TRβ expression plasmid, it was possible to detect specific binding of the TRβ protein to the $^{32}$P-labeled MHC-N oligonucleotides by a gel retardation assay. As a competitor, a 50-fold excess of unlabeled oligonucleotides were added to the binding reactions; both MHC-N and M2 competed, but M1 and M3 did not. This clearly demonstrates that the two G residues in both "A<u>GG</u>TGA" and "A<u>GG</u>ACA" are necessary to constitute the TRβ binding site. The central three nucleotides AGG (that are part of the putative palindrome) are changeable without a significant impact on the receptor binding. This is consistent also with binding data obtained by an avidin-biotin DNA binding assay and a foot-printing pattern on the MHC α gene promoter with the TRs [Flink, et al., J. Biol. Chem. 265: 11233–11237 (1990)]. As expected, cotransfection assays with each construct reveal that both M1 and M3 are completely silent to T$_3$ whereas the M2 reporter retains a T$_3$ response though impaired (see FIG. 3b). These observations support the view that the KHC-TRE is not palindromic, but instead consists of a direct repeat of "AGGTCA"-like half-sites separated by 4 nucleotides.

In view of the results with the MHC-TRE, other previously characterized TREs were similarly reexamined. In a recent report by Petty, et al., in J. Biol. Chem. 265: 7395–7400 (1990), a short 20 bp DNA segment found in the T$_3$ responsive malic enzyme gene promoter was footprinted by the TR. When this sequence is placed in the minimal SV40 promoter it confers T$_3$, responsiveness, and based on the above model, contains a direct repeat motif (see FIG. 3c). In the Figure, malic enzyme TRE corresponds to –XXX to –YYY from a transcription start site (see Petty et al., supra). A thyroid response element found in the murine Maloney Leukemia Virus (MLV) LTR (by both receptor binding and in vivo function; "MLV-LTR"740 is taken from Sap et al. [see rat growth hormone gene TRE [see Brent et al., J. Biol. Chem. 264: 178–182 (1989)]. βRARE corresponds to βRE2 reported in Sucov et al. [Proc. Natl. Acad. Sci. U.S.A. 87: 5392–5398 (1990)].

When the TRE found in the MLV-LTR is placed into the SV40 reporter it confers T$_3$, inducibility. Based on the MHC model, a direct repeat of the "AGGTCA"—like sequence can be identified in these sequences (see FIG. 3c). In contrast, a rat growth hormone (rGH) gene sequence proposed by Brent, et al. supra, as a candidate TRE, fails to confer inducibility to the SV40 reporter (see FIG. 3c). However, as shown below, this sequence fails to interact with the TR in vitro and thus, may not be a bona fide response element.

While both the TRs and RARs are able to bind palindromic TREs [see Umesono, et al., Nature 336: 262–265 (1988); Glass, et al., Cell 54: 313–323 (1988); and Graupner, et al., Nature 340: 653–656 (1989)], the direct repeat TRE is TR specific. To understand the molecular nature of this restriction, the structure of previously characterized natural RAREs was re-evaluated. Recently, one such sequence was identified in the promoter region of the mouse [Sucov, et al., and human RARβ genes [de The, et al., Nature 343: 177–180 (1990)]. Interestingly, this RARE (designated as βRARE) is composed of a direct repeat motif and is selectively activated by the RARβ but not by the TR (Sucov, et al., activated by the RAR but not by the TR (Sucov, et al., supra). To better understand the basis of exclusive recognition and selective response of the direct repeat TRE and RARE motifs, a series of comparative in vitro DNA-binding and functional assays were conducted.

Oligonucleotides listed in FIG. 3 were used as a probe to test specific DNA-binding of the RARα and TRβ in a gel retardation assay. On the βRARE, a faint background binding activity was detected in the mock transfected COS cell extract. The TRβ extract contained a weak, yet detectable binding activity over the background; however, the signal obtained with the RARα extract was dramatically enhanced. In addition to the MHC-TRE, the malic enzyme TRE and MLV-LTR TRE are all high affinity TRβ binding sites, consistent with the previous observations of Glass, et al. [Cell 59: 697–708 (1989)], Sap, et al., [Nature 340: 242–244 (1989)], Petty, et al. [J. Biol. Chem. 265: 7395–7400 (1990)], and Flink, et al. [J. Biol. Chem. 265: 11233–11237 (1990)]. On the other hand, TRβ binds very poorly to the rGH21 probe, which (as described above) also fails to confer T$_3$-dependent transactivation in transfection experiments (FIG. 3c). Finally, no appreciable binding of the RARα protein was seen with any of these TREs. In each case the result obtained from in vivo transactivation and in vitro DNA binding are consistent. Thus, these tandem HREs possess intrinsic differences to impart selective TR or RAR specific binding and activation, and virtually eliminate the possibility of hormonal cross-talk.

Starting from the MHC-TRE (MHC-N), a set of oligonucleotides (see FIG. 4a) were designed to introduce variations in the half-site spacing (MCH+1), the half-site sequence (MHC-T), or both (MHC-R). A single copy of these oligonucleotides was placed in the basal reporter construct ΔSV-CAT (designated by "(−)" in FIG. 4b), giving rise to a set of CAT reporter plasmids together with one encoding TREp. Parallel cotransfections with expression plasmids for TRβ or RARα were performed in CV-1 cells along-with the ΔSV-CAT reporter containing a single copy of the variant HRE. After addition of hormone (RA, 1 μM; $T_3$, 100 nM), the cell extracts were assayed for the CAT activity by measuring the β-galactosidase activity produced by cotransfected pRAS-βGAL. In the figure, numbers in the columns indicate the level of induction of CAT activity by the hormone.

Using the control palindromic TREp reporter, TRβ and RARα elicited a 14 and 9 fold induction, respectively, while the MHC-N confers T, but not RA response. By increasing the spacing by one nucleotide, the $T_3$ response decreases from 10 fold to less than 2 fold, and conversely confers a modest but significant induction by RA (4 fold). In MHC-T the "AGGACA" half-site was corrected to "AGGTCA", resulting in a better $T_3$ response (15 fold) than the wild type (10 fold), while producing only a marginal RA response (2.6 fold). In contrast, increasing the half-site spacing of MHC-T by one nucleotide (to MHC-R) generates an efficient RARE (7.4 fold RA induction), while reciprocally blunting $T_3$ responsiveness (1.3 fold). The position of the nucleotide insertion within the spacer is flexible; the phenotype of another mutant carrying the MHC-T mutation together with an additional G in the middle of the spacer (CAGG to CAGGG) is identical to that of the MHC-R. Thus, half-site spacing is indicated as the determinative parameter since a single nucleotide insertion (MHC-T to MHC-R) is sufficient to interconvert a TRE to an RARE.

Using the mobility shift assay, the DNA-binding capacity of extracts from COS cells expressing TRβ and RARα to these sequences was also tested. The positive TREs (TREp, MHC-N, and MHC-T) showed efficient competition with MHC-T notably better than the wild type. In contrast, the RA response elements (MHC+1, MHC-R, and βRARE) are poor competitors. This pattern is consistent with that of the in vivo activation (FIG. 4). A reciprocal pattern was obtained when the same oligonucleotides were used to compete RARE binding to the $^{32}$P-labeled βRARE. Thus, RA response elements (TREp, βRARE, and MHC-R) are all effective competitors, while MHC-TRE fails to compete at all. Furthermore, MHC-T, which differs by only one nucleotide from MHC-R, also fails to compete efficiently. This provides a striking example of the role of half-site spacing in generating a functional response element. The comparable binding affinity of the MHC-R to that of TREp, together with much weaker affinity of MHC+1 and MHC-T, correlate well with the results from the transfection assays (FIG. 4).

The parallels between in vivo transactivation and in vitro DNA-binding patterns by two distinct receptors strongly supports the conclusion that the TR binds to an "AGGTCA"-like direct repeat with a 4-nucleotide spacer while the RAR recognizes the similar motif but with a spacing of 5 nucleotides.

Recent characterization of a VDRE found in the rat osteocalcin gene promoter [rOST-VDRE; see Demay, et al., J. Biol. Chem. 266: 1008–1013 (1990); and Markose, et al., Proc. Natl. Acad. Sci. U.S.A. 87: 1701–1705 (1990)] revealed the presence of three "AGGTCA" related sequences in a close proximity (5'-CTGGGTGAATG AGGACATTACTGACC-3'; SEQ ID NO:49). The 5' portion of the rOST-VDRE contains a tandem repeat of "GGGTGA" and "AGGACA" and is similar to the MHC-TRE (FIG. 3). Because of the important role of the half-site spacing for TR and RAR selectivity, it was tested to see if this observation might extend to the VDRE in which half-sites are spaced by 3 nucleotides.

Accordingly, a nested set of synthetic hormone response elements were designed by making a direct repeat of "AGGTCA" with a spacer size variation of 3, 4, or 5 residues (FIG. 5a). DR-3, DR-4, and DR-5 each code for perfect tandem repeats of the "AGGTCA" hexamers (indicated by arrows in the figure), separated by 3, 4, and 5 nucleotides, respectively. GDR-3, GDR-4, and GDR-5 are identical to the DR oligonucleotides except that the half-site sequence was changed to "AGAACA", a GRE half-site.

Since DR-4 encodes two copies of "AGGTCA" in direct repeat separated by four nucleotides, it should, in principle, be a TRE. A single nucleotide insertion to create DR-5, with a 5-nucleotide spacer, should be an RARE. Similarly, one nucleotide deletion from the spacer gives rise to DR-3, a VDRE candidate. Oligonucleotides were also synthesized which share identical structures to the DR series, but encode a GRE half-site (AGAACA) instead of AGGTCA, as a further control for sequence specificity (i.e., the GDR series; see FIG. 5a).

The above strategies were used to test both in vivo transactivation and in vitro DNA-binding of these artificial HREs for Twβ, RARα, and VDR. A single copy of the DR or GDR oligonucleotides was cloned at the unique HindIII site present in the basal promoter-CAT construct, ΔSV-CAT, giving rise to DR-3-CAT, DR-4-CAT, DR-5-CAT, GDR-3-CAT, GDR-4-CAT, and GDR-5-CAT reporters. One μg of the indicated reporters ["(−)" refers to ΔSV-CAT] were cotransfected into CV-1 cells with 0.5 μg of an expression plasmid for VDR, TRβ, or RARα. After 36 hours of incubation with the cognate ligands ($VD_3$ and $T_3$, 100 nM; RA, 1 μM), the cells were harvested for CAT assay after normalization with β-galactosidase activity produced from the cotransfected control reporter pRAS-βGAL. The CAT activity obtained through ΔSV-CAT in the absence of ligand was taken as 1 for each of the receptors.

Transfection assays in CV-1 cells revealed that DR-3 is indeed a novel vitamin D3 response element (8.3 fold induction, see FIG. 5b). As predicted, based on the above-described model, a single nucleotide insertion in the spacer from DR-3 (to produce DR4) mutually interconverts the vitamin D3 and T, responses (22 fold induction by T3 through DR-4, FIG. 5c). The half-site mutants GDR-3 and GDR-4 are completely inactive for both the VDR and TR. While DR-5 confers the best RA response (9 fold induction), DR-3 and DR-4 show clear activity (FIG. 5d). As shown below, this is probably a consequence of overexpression of the receptor protein.

These properties of the synthetic DR hormone response elements can be transferred to a different basal promoter such as Herpes simplex virus thymidine Kinase gene promoter.

When the DR reporters are transfected into RA responsive F9 teratocarcinoma stem cells, only DR-5 serves as a functional RARE. Similarly, when the same set of reporters as in FIG. 4 were transfected into F9 cells, only MHC-R (5-nucleotide spacer) and TREp are potent RAREs. In contrast, its RARE antecedents (MHC−N, MHC+1, MHC−

T) are inert. Using βRARE as a probe, a specific protein-DNA complex was detected in extracts prepared from the F9 stem cells, which reveals a DNA-binding pattern identical to that of RARα-transfected COS cell extracts.

Finally, in vitro DNA-binding assays were carried out with COS cell extracts containing one of these receptor proteins. With the DR-3, DR-4, and DR-5 as a labeled probe, a specific protein-DNA complex was observed, which is dependent on the expression of the VDR, TRβ, and RARα protein, respectively, in the cell. These studies parallel the transactivation experiments and indicate that the DR-3, DR-4 and DR-5 sequences represent specific binding response elements for the VDR, TRβ, and RARα, respectively.

While the invention has been described in detail with reference to preferred embodiments thereof, it will be understood that modifications and variations are within the spirit and scope of that which is described and claimed herein.

The invention claimed is:

1. A method of determining whether a test compound has agonist activity for a member of the steroid/thyroid superfamily of receptors, said method comprising:
  (a) culturing cells transformed with a vector for the expression of an indicator protein, in the presence of a member of the steroid/thyroid superfamily of receptors, and in the presence and absence of said test compound, wherein said vector comprises a substantially pure DNA response element operatively linked to a promoter which is not normally subject to transcriptional activation and/or repression by ligand for said member of the steroid/thyroid superfamily and linked operatively for transcription of a gene encoding said indicator protein, so as to confer transcriptional activation and/or repression activity on said promoter in the presence of a compound having agonist activity,
  wherein said DNA response element comprises at least two half sites, each separated by three, four, or five spacer nucleotides, wherein each half site is independently selected from -AGGTCA-, -GGGTTA-, -GGGTGA-, -AGGTGA-, -AGGACA-, -GGGGCA-, or -GGGTCA-, -AGGTCC-, -GGTTCA-, -AGTTCA-, or -AGGGCA-;

wherein said three spacer nucleotides are selected from -AGG-, -ATG-, -ACG-, or -CGA-; and thereafter (b) comparing the amount of said indicator protein expressed in the presence of said test compound to the amount of said indicator protein expressed in the absence of said test compound.

2. A method according to claim 1, wherein said DNA response element comprises the sequence:
5'-AGGTCA-AGG-AGGTCA-3' (SEQ ID NO:34).

3. A method according to claim 1, wherein said four spacer nucleotides are selected from -CAGG-, -GGGG-, or -TTTC-.

4. A method according to claim 3, wherein said DNA response element comprises the sequence:
5'-AGGTCA-CAGG-AGGTCA-3' (SEQ ID NO:38), or
5'-AGGTGA-CAGG-AGGTCA-3' (SEQ ID NO:39).

5. A method according to claim 1, wherein said five spacer nucleotides are selected from -CCAGG-, -ACAGG-, -CCGAA-, -CTGAC-, or -TTGAC-.

6. A method according to claim 5, wherein said DNA response element comprises the sequence:
5'-AGGTGA-ACAGG-AGGTCA-3' (SEQ ID NO:44),
5'-AAGCTTAAG-GGTTCA-CCGAA-AGTTCA-CTCAGCTT-3' (SEQ ID NO:7),
5'-AAGCTTAAG-GGTTCA-CCGAA-AGTTCA-CTCGCATAGCTT-3' (SEQ ID NO:6), or
5'-AAGCTTAAG-GGTTCA-CCGAA-AGTTCA-CTCGCATATATTAGCTT-3' (SEQ ID NO:5).

7. A method of determining whether a test compound has antagonist activity for a member of the steroid/thyroid superfamily of receptors, said method comprising:

(a) culturing cells transformed with a vector for the expression of an indicator protein, in the presence of (i) a member of the steroid/thyroid superfamily of receptors, and (ii) an agonist for said member; and in the further presence and absence of said test compound, wherein said vector comprises a substantially pure DNA response element operatively linked to a promoter which is not normally subject to transcriptional activation and/or repression by ligand for said member of the steroid/thyroid superfamily and linked operatively for transcription of a gene encoding said indicator protein, so as to confer transcriptional activation and/or repression activity on said promoter in the presence of said agonist, wherein said DNA response element comprises at least two half sites, each separated by three, four, or five spacer nucleotides, wherein each half site is independently selected from -AGGTCA-, -GGGTTA-, -GGGTGA-, -AGGTGA-, -AGGACA-, -GGGGCA-, or -GGGTCA-, -AGGTCC-, -GGTTCA-, -AGTTCA-, or -AGGGCA-;

wherein said three spacer nucleotides are selected from -AGG-, -ATG-, -ACG-, or -CGA-; and thereafter (b) comparing the amount of said indicator protein expressed in the presence of said test compound to the amount of said indicator protein expressed in absence of said test compound.

8. A method according to claim 7, wherein said DNA response element comprises the sequence:
5'-AGGTCA-AGG-AGGTCA-3' (SEQ ID NO:34).

9. A method according to claim 7, wherein said four spacer nucleotides are selected from -CAGG-, -GGGG-, or -TTTC-.

10. A method according to claim 9, wherein said DNA response element comprises the sequence:
5'-AGGTCA-CAGG-AGGTCA-3' (SEQ ID NO:38), or
5'-AGGTGA-CAGG-AGGTCA-3' (SEQ ID NO:39).

11. A method according to claim 7, wherein said five spacer nucleotides are selected from -CCAGG-, -ACAGG-, -CCGAA-, -CTGAC-, or -TTGAC-.

12. A method according to claim 11, wherein said DNA response element comprises the sequence:
5'-AGGTGA-ACAGG-AGGTCA-3' (SEQ ID NO:44),
5'-AAGCTTAAG-GGTTCA-CCGAA-AGTTCA-CTCAGCTT-3' (SEQ ID NO:7),
5'-AAGCTTAAG-GGTTCA-CCGAA-AGTTCA-CTCGCATAGCTT-3' (SEQ ID NO:6), or
5'-AAGCTTAAG-GGTTCA-CCGAA-AGTTCA-CTCGCATATATTAGCTT-3' (SEQ ID NO:5).

* * * * *